United States Patent [19]
Faulks et al.

[11] Patent Number: 5,919,179
[45] Date of Patent: Jul. 6, 1999

[54] ABSORBENT ARTICLE INCORPORATING AN ABSORBENT ASSEMBLY

[75] Inventors: Michael John Faulks, Neenah; Daniel Robert Schlinz, Greenville; Paul John Serbiak, Appleton, all of Wis.

[73] Assignee: Kimberly-Clark Worldwide, Inc., Neenah, Wis.

[21] Appl. No.: 08/772,209

[22] Filed: Dec. 20, 1996

[51] Int. Cl.$^6$ .............................. A61F 13/15; A61F 13/20
[52] U.S. Cl. ........................................................ 604/385.2
[58] Field of Search ................................ 604/378, 385.1, 604/385.2, 386

[56] References Cited

U.S. PATENT DOCUMENTS

| | | | |
|---|---|---|---|
| Re. 33,106 | 11/1989 | Beckestrom | 604/385.2 |
| 2,532,029 | 11/1950 | Medoff | 128/287 |
| 2,545,674 | 3/1951 | Ralph | 128/287 |
| 2,575,163 | 11/1951 | Donovan | 128/287 |
| 2,575,164 | 11/1951 | Donavan | 128/287 |
| 2,893,393 | 7/1959 | Pressley | 128/287 |
| 2,956,564 | 10/1960 | Ohara | 128/287 |
| 3,386,442 | 6/1968 | Sabee | 128/287 |
| 3,901,236 | 8/1975 | Assarsson et al. | 128/284 |
| 4,076,663 | 2/1978 | Masuda et al. | 260/17.4 GC |
| 4,286,082 | 8/1981 | Tsubakimoto et al. | 526/240 |
| 4,381,781 | 5/1983 | Sciaraffa et al. | 604/372 |
| 4,486,192 | 12/1984 | Sigl | 604/385 |
| 4,490,148 | 12/1984 | Beckestrom | 604/385 |
| 4,585,448 | 4/1986 | Enloe | 604/378 |

(List continued on next page.)

FOREIGN PATENT DOCUMENTS

| | | |
|---|---|---|
| 0 243 013 A1 | 10/1987 | European Pat. Off. ......... A41B 13/02 |
| 0 251 332 B1 | 1/1988 | European Pat. Off. ......... A61F 13/15 |
| 0 312 071 A2 | 4/1989 | European Pat. Off. ......... A41B 13/02 |
| 0 324 133 B1 | 8/1989 | European Pat. Off. ......... A61F 13/15 |
| 0 329 160 B1 | 8/1989 | European Pat. Off. ......... A61F 13/15 |
| 0 376 022 B1 | 7/1990 | European Pat. Off. ......... A61F 13/15 |
| 0 386 815 A2 | 9/1990 | European Pat. Off. ......... A61F 13/15 |
| 0 403 832 B1 | 12/1990 | European Pat. Off. ......... A61F 13/15 |
| 0 404 648 B1 | 12/1990 | European Pat. Off. ......... A61F 13/15 |
| 0 433 951 A2 | 6/1991 | European Pat. Off. ......... A61F 13/15 |
| 7-184955 | 7/1995 | Japan ............... A61F 13/15 |
| 7-184954 | 9/1995 | Japan ............... A61F 13/15 |
| 92/06027 | 8/1992 | South Africa . |
| 2 262 873 | 7/1993 | United Kingdom ............ A61F 13/15 |
| 2 265 550 | 10/1993 | United Kingdom ............ A61F 13/15 |
| 2 265 834 | 10/1993 | United Kingdom ............ A61F 13/15 |
| 2 266 055 | 10/1993 | United Kingdom ............ A61F 13/15 |
| 2 266 225 | 10/1993 | United Kingdom ............ A61F 13/15 |
| 2 266 444 | 11/1993 | United Kingdom ............ A61F 13/15 |
| 2 268 389 | 1/1994 | United Kingdom ............ A61F 13/15 |
| 2 280 374 | 2/1994 | United Kingdom ............ A62F 13/15 |
| 2 270 247 | 3/1994 | United Kingdom ............ A61F 13/15 |
| 2 278 993 | 12/1994 | United Kingdom ............ A61F 13/15 |
| WO 91/08717 A2 | 6/1991 | WIPO .............. A61F 13/15 |
| WO 92/07533 A1 | 5/1992 | WIPO .............. A61F 13/15 |

(List continued on next page.)

*Primary Examiner*—Mickey Yu
*Assistant Examiner*—Tram A. Nguyen

[57] ABSTRACT

Disclosed is a disposable absorbent article comprising an outer cover and an absorbent assembly joined to said outer cover. The absorbent assembly comprises a liquid impermeable member having a pair of laterally opposed side margins. An absorbent core is joined to said liquid impermeable member between said laterally opposed side margins of said liquid impermeable member. Both the outer cover and the absorbent assembly define a front portion, a rear portion, and an intermediate portion which interconnects the front and rear portions. The lateral width of the absorbent assembly in said intermediate portion is defined by the laterally opposed side margins of said liquid impermeable member. The lateral width of said laterally opposed side margins of said liquid impermeable member in the intermediate portion of said absorbent assembly is greater than the lateral width of the intermediate portion of the outer cover.

34 Claims, 6 Drawing Sheets

U.S. PATENT DOCUMENTS

| | | | |
|---|---|---|---|
| 4,643,728 | 2/1987 | Karami | 604/385 A |
| 4,657,539 | 4/1987 | Hasse | 605/385 A |
| 4,662,877 | 5/1987 | Williams | 604/385 A |
| 4,695,278 | 9/1987 | Lawson | 604/385 A |
| 4,699,823 | 10/1987 | Kellenberger et al. | 428/219 |
| 4,704,116 | 11/1987 | Enloe | 604/385 A |
| 4,713,068 | 12/1987 | Wang et al. | 604/366 |
| 4,738,677 | 4/1988 | Foreman | 604/385 R |
| 4,743,246 | 5/1988 | Lawson | 604/385 A |
| 4,753,646 | 6/1988 | Enloe | 604/385 R |
| 4,758,239 | 7/1988 | Yeo et al. | 604/366 |
| 4,770,656 | 9/1988 | Proxmire et al. | 604/393 |
| 4,795,454 | 1/1989 | Dragoo | 604/385.2 |
| 4,816,025 | 3/1989 | Foreman | 604/385.2 |
| 4,818,600 | 4/1989 | Braun et al. | 428/290 |
| 4,822,435 | 4/1989 | Igaue et al. | 156/164 |
| 4,828,556 | 5/1989 | Braun et al. | 604/365 |
| 4,834,740 | 5/1989 | Suzuki et al. | 604/385.2 |
| 4,846,823 | 7/1989 | Enloe | 605/385.2 |
| 4,846,825 | 7/1989 | Enloe et al. | 604/385.1 |
| 4,861,652 | 8/1989 | Lippert et al. | 428/284 |
| 4,883,480 | 11/1989 | Huffman et al. | 604/385.1 |
| 4,892,528 | 1/1990 | Suzuki et al. | 604/385.2 |
| 4,904,251 | 2/1990 | Igaue et al. | 604/385.2 |
| 4,916,005 | 4/1990 | Lippert et al. | 428/192 |
| 4,938,754 | 7/1990 | Mesek | 604/385.2 |
| 4,938,755 | 7/1990 | Foreman | 604/385.2 |
| 4,998,929 | 3/1991 | Bjorksund et al. | 604/385.2 |
| 5,019,066 | 5/1991 | Freeland et al. | 604/385.2 |
| 5,026,364 | 6/1991 | Robertson | 604/385.1 |
| 5,028,224 | 7/1991 | Pieper et al. | 425/80.1 |
| 5,032,120 | 7/1991 | Freeland et al. | 604/385.2 |
| 5,061,261 | 10/1991 | Suzuki et al. | 604/385.2 |
| 5,064,489 | 11/1991 | Ujimoto et al. | 156/164 |
| 5,080,658 | 1/1992 | Igaue et al. | 605/385.2 |
| 5,085,654 | 2/1992 | Buell | 604/370 |
| 5,114,420 | 5/1992 | Igaue et al. | 604/385.2 |
| 5,167,653 | 12/1992 | Igaue et al. | 604/385.2 |
| 5,176,672 | 1/1993 | Bruemmer et al. | 604/385.1 |
| 5,221,277 | 6/1993 | Beplate | 604/394 |
| 5,246,432 | 9/1993 | Suzuki et al. | 604/385.2 |
| 5,263,948 | 11/1993 | Karami et al. | 604/383 |
| 5,275,590 | 1/1994 | Huffman et al. | 604/385.2 |
| 5,292,316 | 3/1994 | Suzuki | 604/385.2 |
| 5,304,159 | 4/1994 | Tanji et al. | 604/385.2 |
| 5,304,160 | 4/1994 | Igaue et al. | 604/385.2 |
| 5,330,598 | 7/1994 | Erdman et al. | 156/164 |
| 5,342,342 | 8/1994 | Kitaoka | 604/385.2 |
| 5,342,344 | 8/1994 | Lancaster et al. | 604/386 |
| 5,344,516 | 9/1994 | Tanji et al. | 156/164 |
| 5,360,422 | 11/1994 | Brownlee et al. | 604/385.2 |
| 5,364,382 | 11/1994 | Latimer et al. | 604/378 |
| 5,399,176 | 3/1995 | Chen | 604/385.1 |
| 5,429,629 | 6/1995 | Latimer et al. | 604/378 |
| 5,482,765 | 1/1996 | Bradley et al. | 428/286 |
| 5,569,227 | 10/1996 | Vandemoortele et al. | 604/382 |
| 5,865,825 | 2/1999 | Schlinz | 604/385.2 |
| B1 4,636,207 | 11/1989 | Buell | 604/370 |

FOREIGN PATENT DOCUMENTS

| | | | |
|---|---|---|---|
| WO 92/09253 A2 | 6/1992 | WIPO | A61F 13/56 |
| WO 92/12648 A1 | 8/1992 | WIPO | A41B 13/04 |
| WO 92/22271 A1 | 12/1992 | WIPO | A61F 13/15 |
| WO 93/00059 A1 | 1/1993 | WIPO | A61F 13/15 |
| WO 93/03698 A1 | 3/1993 | WIPO | A61F 13/15 |
| WO 93/05742 A1 | 4/1993 | WIPO | A61F 13/15 |
| WO 93/09739 A1 | 5/1993 | WIPO | A61F 13/15 |
| WO 93/12746 A1 | 7/1993 | WIPO | A61F 13/15 |
| WO 93/23000 A1 | 11/1993 | WIPO | A61F 13/74 |
| WO 94/18927 A1 | 9/1994 | WIPO | A61F 13/15 |
| WO 95/07063 A1 | 3/1995 | WIPO | A61F 13/15 |

ABSORBENT ARTICLE INCORPORATING AN ABSORBENT ASSEMBLY

FIELD OF THE INVENTION

The present invention relates to an absorbent article. More particularly, the present invention relates to an absorbent article which incorporates a distinctive absorbent assembly.

BACKGROUND OF THE INVENTION

Conventional absorbent articles, such as disposable diapers, have been constructed with various types of mechanical containment features. For example, known absorbent articles incorporate elasticized waistbands and elasticized legbands aimed at forming a tight seal around the waist and legs of a wearer to mechanically prevent leakage from the absorbent articles. It has also been described to employ various forms of elasticized containment flaps and/or waste caps which are intended to project from the body-contacting surface of such absorbent articles to stop the flow of waste materials along the body-contacting surface of the absorbent articles before such materials can leak from the absorbent articles.

Conventional containment flaps and/or waste caps often take the form of separate elements which are attached to various portions of conventional absorbent articles. Such separately attached containment flaps and/or waste caps thereby involve a seam formed between the containment flap and/or waste cap and the conventional absorbent article. The presence of such seams has been found to both complicate the manufacturing process and, if improperly formed, to allow leakage of excreted wastes from the absorbent article employing such containment flaps and/or waste caps. As a result, there is a continued need for improved mechanical containment structures for use in connection with absorbent articles.

BRIEF DESCRIPTION OF THE INVENTION

The present invention relates to a disposable absorbent article having a longitudinal length dimension, a lateral width dimension, a front portion, a rear portion, and an intermediate portion which interconnects said front and rear portions. The article comprises an outer cover and an absorbent assembly joined to said outer cover. The outer cover has a longitudinal length dimension, a lateral width dimension, a front portion, a rear portion, and an intermediate portion that interconnects said front and rear portions. At least one of said front and rear portions of said outer cover has a lateral width dimension greater than a lateral width dimension of said intermediate portion of said outer cover to define ear portions. The absorbent assembly has a longitudinal length dimension, a lateral width dimension, a front portion, a rear portion, and an intermediate portion which interconnects said front and rear portion. The absorbent assembly comprises a liquid impermeable member having a pair of laterally opposed side margins which define the lateral width dimension of said absorbent assembly in said intermediate portion of said absorbent assembly. The lateral width of said absorbent assembly in said intermediate portion of said absorbent assembly is greater than the lateral width of said outer cover in said intermediate portion of said outer cover. The absorbent assembly further comprises an absorbent core joined to said liquid impermeable member between said laterally opposed side margins of said liquid impermeable member.

In particular aspects of the invention, the laterally opposed side margins of said liquid impermeable member are defined by longitudinal fold lines which define folded portions. The folded portions have longitudinal end portions, an intermediate portion between said longitudinal end portions and a distal edge. The longitudinal end portions are joined to the absorbent assembly in the front and rear portion of said absorbent assembly intermediate the lateral width dimension of said absorbent assembly.

In another aspect, the absorbent core comprises a retention portion having a longitudinal length dimension defined by end margins and a lateral width dimension defined by side margins. The retention portion is for absorbing and retaining liquid. The absorbent core further comprises a bodyside liner which at least partially covers said retention portion. The bodyside liner may extend laterally beyond the longitudinal side margins of said retention portion by at least about 12 millimeters to define stiffening elements. Optionally, the retention portion is at least partially enclosed by an overwrap layer located such that the bodyside liner partially covers said retention portion and said overwrap layer. The overwrap layer and said bodyside liner may extend laterally beyond side margins of said retention portion by at least about 12 millimeters to define stiffening elements. The stiffening elements are suitably unjoined to said liquid impermeable member so as to be movable with respect thereto.

The various aspects of the invention can provide a disposable absorbent article that can more reliably and effectively assist in the mechanical containment of excreted body wastes during use. Further, the improved mechanical containment may be achieved in an article which is relatively less complicated to manufacture than certain conventional articles employing mechanical containment features.

BRIEF DESCRIPTION OF THE DRAWINGS

The invention will be more fully understood and further advantages will become apparent when reference is made to the following detailed description and accompanying drawings in which.

DETAILED DESCRIPTION OF THE PREFERRED EMBODIMENT

The present invention will be described herein in relationship to a disposable absorbent article. Such articles can be placed in proximity to the body of a wearer to absorb and contain various exudates discharged from the body, and are intended to be discarded after a limited period of use. The articles are not intended to be laundered or otherwise restored for re-use. While the present description will particularly be made in the context of a diaper article, it should be understood that the present invention is also applicable to other articles, such as adult incontinence garments, sanitary napkins, children's training pants, and the like.

In addition, the invention will be described in the context of its various configurations and aspects. It should be appreciated that alternative arrangements of the invention can comprise any combination which includes one or more of the various configurations and aspects of the invention.

Figure 1:
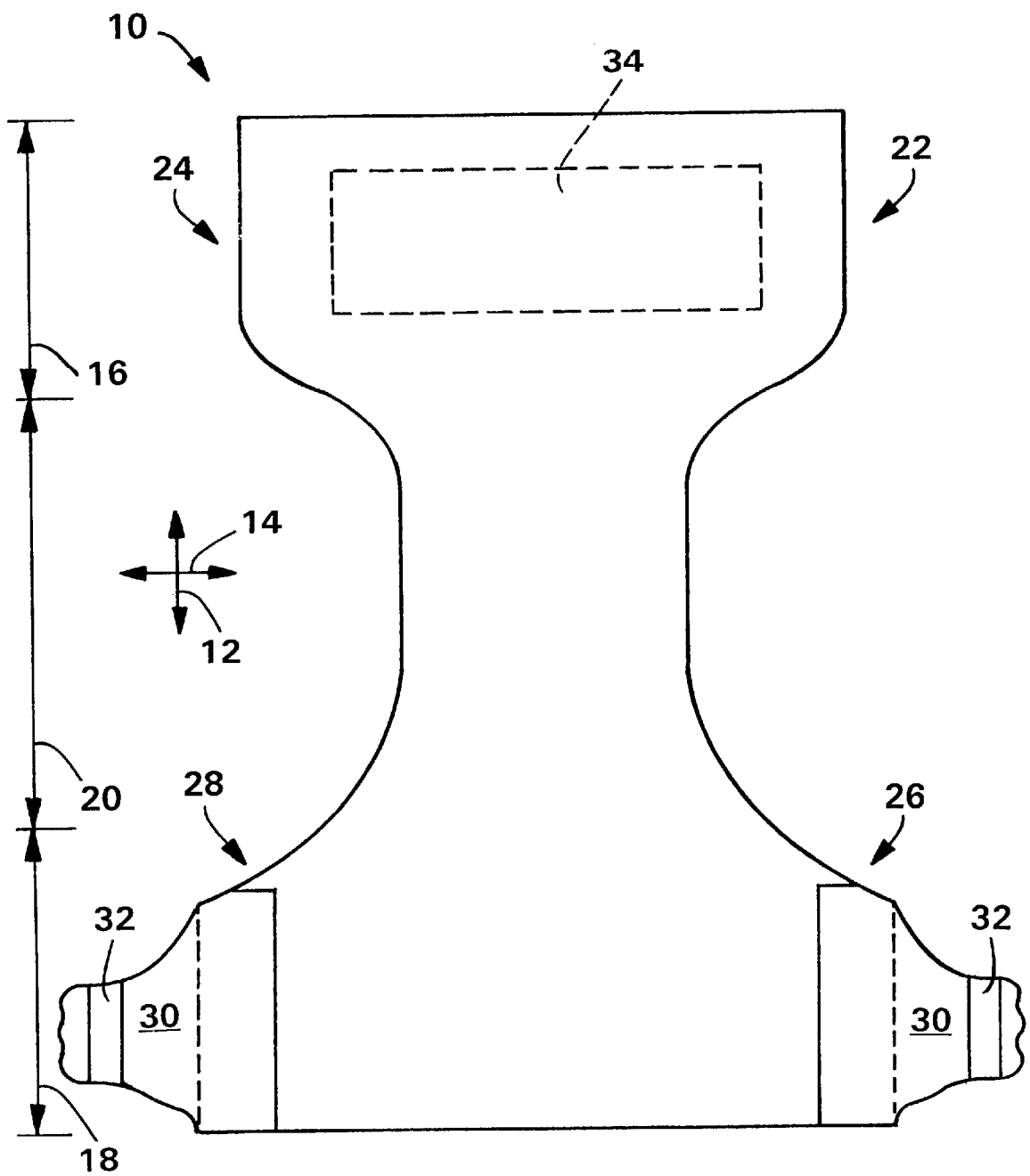
FIG. 1 representatively shows a top plan view of an outer cover of an article according to the present invention.

The present invention relates to disposable absorbent articles having a longitudinal length dimension, a lateral width dimension, a front portion, a rear portion, and an intermediate portion which interconnects said front and rear portions. The article comprises an outer cover and an absorbent assembly joined to said outer cover. With reference to FIG. 1, the outer cover 10 has a longitudinal length dimension in the direction 12 and a lateral width dimension in the direction 14. The outer cover 10 further includes a front portion 16, a rear portion 18, and an intermediate portion 20 which interconnects the front portion 16 and the rear portion 18. At least one of the front and rear portions of said outer cover has a lateral width dimension greater than a lateral width dimension of the intermediate portion of said outer cover to define ear portions. The outer cover may define ears in either or both of the front portion and rear portion. In the illustrated embodiment, outer cover 10 defines ear portions 22 and 24 in front portion 16 and ear portions 26 and 28 in said rear portion 18.

The outer cover further comprises fastening means joined to said outer cover for fastening said article about the waist of a wearer. With reference to FIG. 1, outer cover 10 includes fastening tabs 30 which, in the illustrated embodiment further include first fastening elements 32 adapted to releasably engage second fastening element 34 located in the front portion 16.

The outer cover 10 may be manufactured from any flexible material which is compliant and will readily conform to the general shape and contour of a wearers body. The material from which the outer cover 10 is formed may be either liquid permeable or liquid impermeable and may be either permeable or impermeable to water vapor. Examples of materials of which the outer cover can be fabricated include polymeric films, woven or knitted fabrics, nonwoven fabrics, foams, and the like. Suitable films may be either water vapor permeable or water vapor impermeable. A suitable water vapor impermeable film is a polyethylene or polypropylene film having a thickness of about 0.012 millimeters (0.5 mil) to about 0.051 millimeters (2.0 mil). A water vapor permeable film is, for example, a microporous film commercially available from Mitsui Toatsu Chemicals Inc. under the trade designation PMP-1 or an XKO-8044 polyolefin film available from 3M Company of Minneapolis, Minn. The polymeric film may be used separately or may comprise a woven or nonwoven fibrous web layer joined to the polymeric films. The woven or nonwoven fibrous web layer suitably imparts a clothlike feel to the outer surface of the film. For example, a clothlike outer cover may be composed of an approximately 0.5 ounce per square yard (about 17 grams per square meter) basis weight, polypropylene spunbond fabric which is laminated and thermally bonded to a stretch-thinned polypropylene film having a thickness of about 0.0006 inch (about 0.015 millimeter) and a film basis weight of about 14.5 grams per square meter. Such a material and a method for its manufacture is suitably described in U.S. patent application Ser. No. 08/997,800 filed Dec. 29, 1992, in the name of McCormick et al. (Attorney Docket No. 9945).

Similarly, the outer cover may be formed from a woven or nonwoven fabric which may be treated to impart a desirable degree of liquid impermeability and/or impermeability to water vapor. Suitable nonwoven materials include spunbond materials and meltblown materials. One preferred material from which the outer cover 10 may be fabricated is a composite material of spunbond/meltblown/spunbond fibers (SMS). One specific material from which the outer cover 10 can be fabricated is a liquid impermeable and vapor permeable SMS material having a basis weight of about 50 grams per square meter (gsm). The SMS is suitably formed from a meltblown polypropylene layer which has a basis weight of about 17 gsm and which is positioned between two spunbond polyethylene/polypropylene layers, each of which has a basis weight of about 17 gsm. The meltblown layer may comprise up to about 5 weight polybutylene commercially available from the Shell Chemical Company under the trade designation DP8911. Polypropylene is suitably commercially available from Exxon Chemical under the trade designation 3546G. The spunbond layers include up to about 4 weight percent of a 50 percent concentration of titanium dioxide pigment commercially available from Ampacet under the trade designation Ampacet 41438. The remainder of the spunbond layers comprise a 3 weight percent polyethylene and 97 weight percent polypropylene copolymer which is commercially available from Shell Chemical under the trade designation 6D43. The meltblown layer provides from about 25 to about 35 weight percent of the SMS laminate material. This material has a water vapor transmission rate (WVTR) of about 5,000 grams per square meter per 24 hours.

Suitable materials from which the outer cover 10 can be fabricated are described in commonly owned, U.S. patent application Ser. No. 08/223,210 filed Apr. 5, 1994, in the name of Bradley et al. now U.S. Pat. No. 5,482,765. Other suitable materials for use as outer cover 10 include those described in U.S. Pat. No. 4,713,068 issued Dec. 15, 1987, to Wang et al.; U.S. Pat. No. 4,758,239 issued Jul. 19, 1988, to Yeo et al.; U.S. Pat. No. 4,818,600 issued Apr. 4, 1989, to Braun et al.; and U.S. Pat. No. 4,828,556 issued May 9, 1989, to Braun et al., the disclosures of which are herein incorporated by reference to the extent they are consistent herewith.

As will be described in greater detail below, the absorbent articles of the present invention further include an absorbent assembly joined to said outer cover. The absorbent assembly includes a liquid impermeable member and an absorbent core. Depending upon the specific properties desired for the absorbent article, the outer cover and liquid impermeable member are selected to provide the desired properties. For example, if the liquid impermeable member is water vapor permeable, and water vapor permeability is desired for the absorbent article, it will generally be desirable to select a material which is water vapor permeable for the outer cover material.

It is often desired that the material from which the outer cover is fabricated be water vapor permeable. Water vapor permeability is suitably quantified by reference to the Water Vapor Transmission Rate of the material. The method by which the WVTR for a given material is determined is described in connection with the examples. The outer cover suitably has a WVTR of about 200 to about 8000 or more grams per square meter per 24 hours, alternatively of from about 500 to about 5000 grams per square meter per 24 hours.

Suitable fastening means for use in connection with the outer cover are known to those skilled in the art. Suitable fastening means include adhesive fasteners, as well as mechanical fasteners such as hook-and-loop fasteners, snaps, buttons, and the like. In the illustrated embodiment, the fastening means includes fastening tabs 30 including first fastening element 32. First fastening element 32 suitably comprises a hook or a loop component of a hook or loop fastener. A second fastening element 34 is associated with the outer cover and is adapted to releasably engage with the first fastening element 32. For example, the first fastening element may comprise a hook material, and the second fastening element may comprise a loop material engageable with the hook material. Hook materials suitable for use in the present invention include those materials commercially available from Velcro Group Company under the trade designation CFM 29-1029 or CFM 29-1058. Loop materials suitable for use in the present invention include those knitted loop materials commercially available from Guilford Mills under the trade designation CCK 34922, Style Number 36871. Suitable loop materials may also include nonwoven materials such as those described in commonly owned copending U.S. patent application entitled "Pattern-Unbonded Nonwoven Web and Process for Making the Same" filed Nov. 22, 1996, in the name of Stokes et al. (Attorney Docket Number 12,232).

The fastening tabs 30 may be formed from any material capable of performing the function of a fastening tab. That is, of attaching the disposable absorbent article about the waist of a wearer. For example, the fastening tab may be formed from the same materials as the outer cover 10. In one specific embodiment, the fastening tab is formed from a material which is elastic and capable of stretching in at least direction 14 and, is capable of stretching at least about to 200 percent of its relaxed length and, after stretching, to about 200 percent, to return to approximately its relaxed length.

Figure 2:
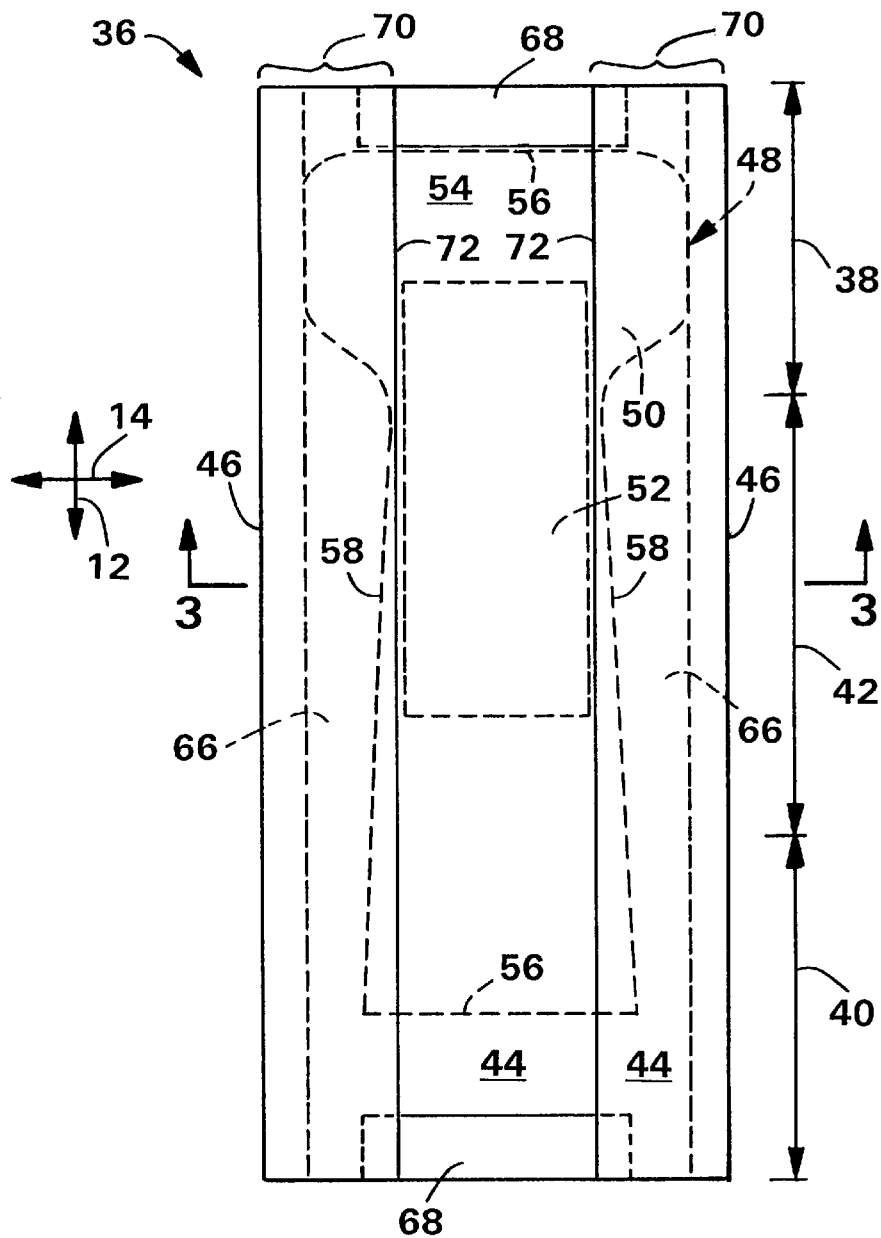
FIG. 2 representatively shows a top plan view of an absorbent assembly of the present invention.

The disposable absorbent article further includes an absorbent assembly joined to said outer cover. With reference to FIG. 2, absorbent assembly 36 is illustrated. The absorbent assembly 36 has a longitudinal length dimension in the direction 12 and a lateral width dimension in the direction 14. Further, absorbent assembly 36 defines a front portion 38, a rear portion 40 and an intermediate portion 42 which interconnects said front and rear portions. The absorbent assembly 36 includes a liquid impermeable member 44, having a pair of laterally opposed side margins 46 which define the lateral width of the absorbent assembly in the intermediate portion of the absorbent assembly in direction 14. The lateral width of absorbent assembly 36 in at least a portion of its intermediate portion 42 is greater than the lateral width of the outer cover 10 in at least a portion of its intermediate portion 20. The absorbent assembly 36 further includes an absorbent core 48 joined to liquid impermeable member 44 between the laterally opposed side margins 46 of liquid impermeable member 44. In the illustrated embodiment, absorbent core 48 includes retention portion 50, surge management portion 52, and a bodyside liner 54 which at least partially covers retention portion 50. The retention portion 50 is designed to absorb and retain liquids and has a longitudinal length dimension in the direction 12 defined by end margins 56 and a lateral width dimension in the direction 14 defined by side margins 58.

Figure 3:
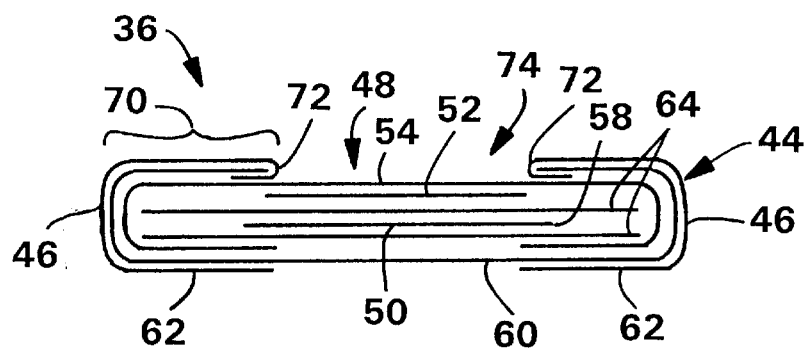
FIG. 3 representatively shows a schematic cross-sectional view taken along line 3—3 of FIG. 2.

As can be seen in greater detail from reference to FIG. 3, which is a schematic cross sectional view taken along line 3—3 of FIG. 2, the liquid impermeable member 44 is, in the illustrated embodiment, comprised of a first liquid impermeable material 60, having a body contacting material 62 joined thereto. As can further be seen from reference to FIGS. 2 and 3, retention portion 50 is enclosed by overwrap layers 64. The bodyside liner 54 and overwrap layers 64 both extend laterally, in the direction 14, beyond the side margins 58 of retention portion 50 to define stiffening elements 66. Stiffening elements 66 are defined by those portions of bodyside liner 54 and/or overwrap layers 64 which extend laterally beyond the side margins 58 of retention portion 50. As illustrated in FIGS. 2 and 3, the stiffening elements may have a width dimension in direction 14 which varies along the length of retention portion 50. It is desired that the stiffening elements have a maximum width dimension at some point along their length of at least about 12 millimeters, alternatively of at least about 15 millimeters, alternatively of from about 12 millimeters to about 80 millimeters. While the absorbent assembly 36 is joined, directly or indirectly to the outer cover 10, it is often desirable that portions of the stiffening elements 66 be unjoined (not directly joined) to the liquid impermeable member 44 so as to be movable with respect thereto.

In the embodiments illustrated in FIGS. 2 and 3, absorbent assembly 36 further includes waist elastic member 68.

As can best be seen by reference to FIG. 3, laterally opposed side margins 46 of said liquid impermeable member 44 are defined by folding liquid impermeable member 44 around stiffening elements 66 to form folded portion 70. Folded portion 70 has longitudinal end portions, an intermediate portion between said longitudinal end portions, and a distal edge 72. The longitudinal end portions of folded portion 70 are joined to the absorbent assembly 36 in said front and rear portions of said absorbent assembly intermediate the lateral width dimension of said absorbent assembly 36. The longitudinal end portions of folded portion 70 generally correspond to the front portion 38 and rear portion 40 of absorbent assembly 36. Similarly, the intermediate portion of said folded portion 70 generally corresponds to the intermediate portion 42 of absorbent assembly 36. At least a portion of distal edge 72 is free to move relative to said absorbent assembly (unattached) in at least a portion of the intermediate portion of said folded portion 70 to thereby form a containment pocket 74.

Figure 4:
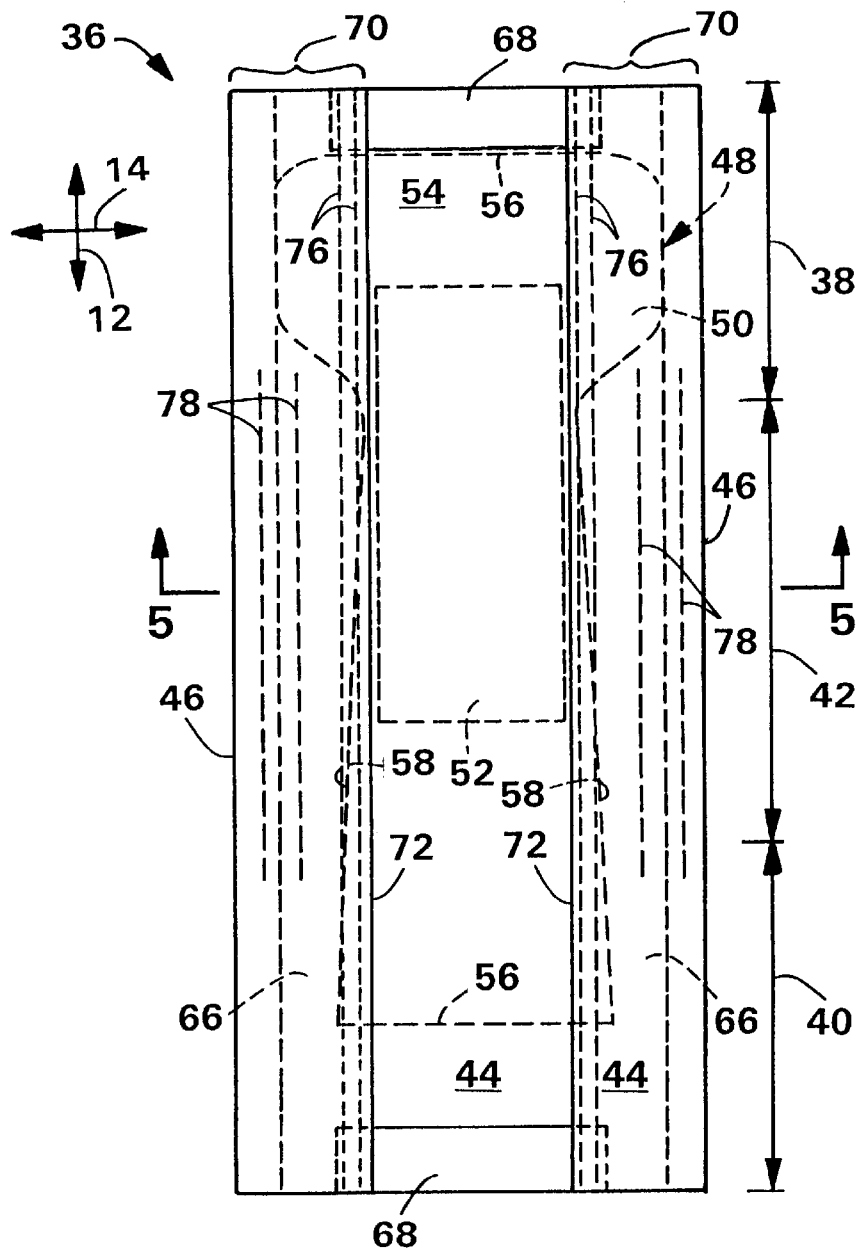
FIG. 4 representatively shows a top plan view of the absorbent assembly of FIG. 2 further comprising various elastic elements.

FIG. 4 is identical to FIG. 2 with the exception that FIG. 4 illustrates various elastic members incorporated into absorbent assembly 36. Similarly, FIG. 5 is identical to FIG. 3 with the exception that it also illustrates various elastic members incorporated into absorbent assembly 36.

Figure 5:
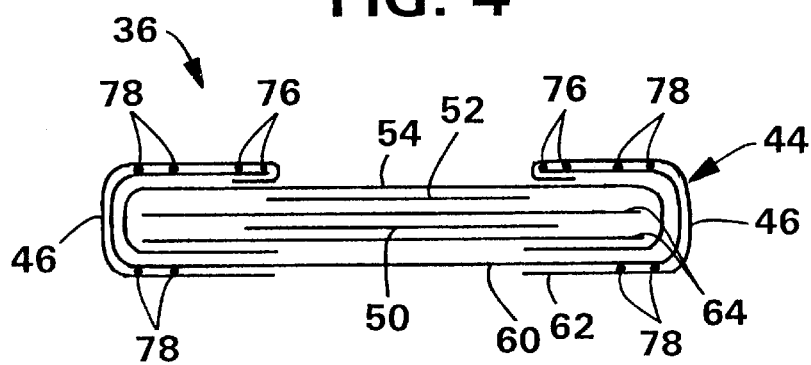
FIG. 5 representatively shows a schematic cross sectional view taken along line 5—5 of FIG. 4.

With reference to FIGS. 4 and 5, absorbent assembly 36 further comprises distal elastic members 76 located adjacent distal edge 72 for elasticizing distal edge 72. Distal elastic members 76 are, suitably, attached to distal edge 72 of folded portion 70 in a tensioned state so that, upon relaxation, distal edge 72 is gathered. This gathering causes portions of distal edge 72 which are unattached to the absorbent assembly in the intermediate portion of folded portion 70 to be located above and spaced away from bodyside liner 54 to thereby further define containment pockets 74.

The absorbent assembly 36 further includes elastic members 78 operatively associated with liquid impermeable member 44 to gather liquid impermeable member 44 along its length. This, in combination with distal elastic members 76, causes the absorbent assembly 36 to form a bowed or cupped configuration. Elastic members may, for example, be joined to either or both of first liquid impermeable material 60 or body contacting material 62. Elastic members 78 also perform a gasketing function by contracting to form a seal around the legs of a wearer in use.

Figure 6:
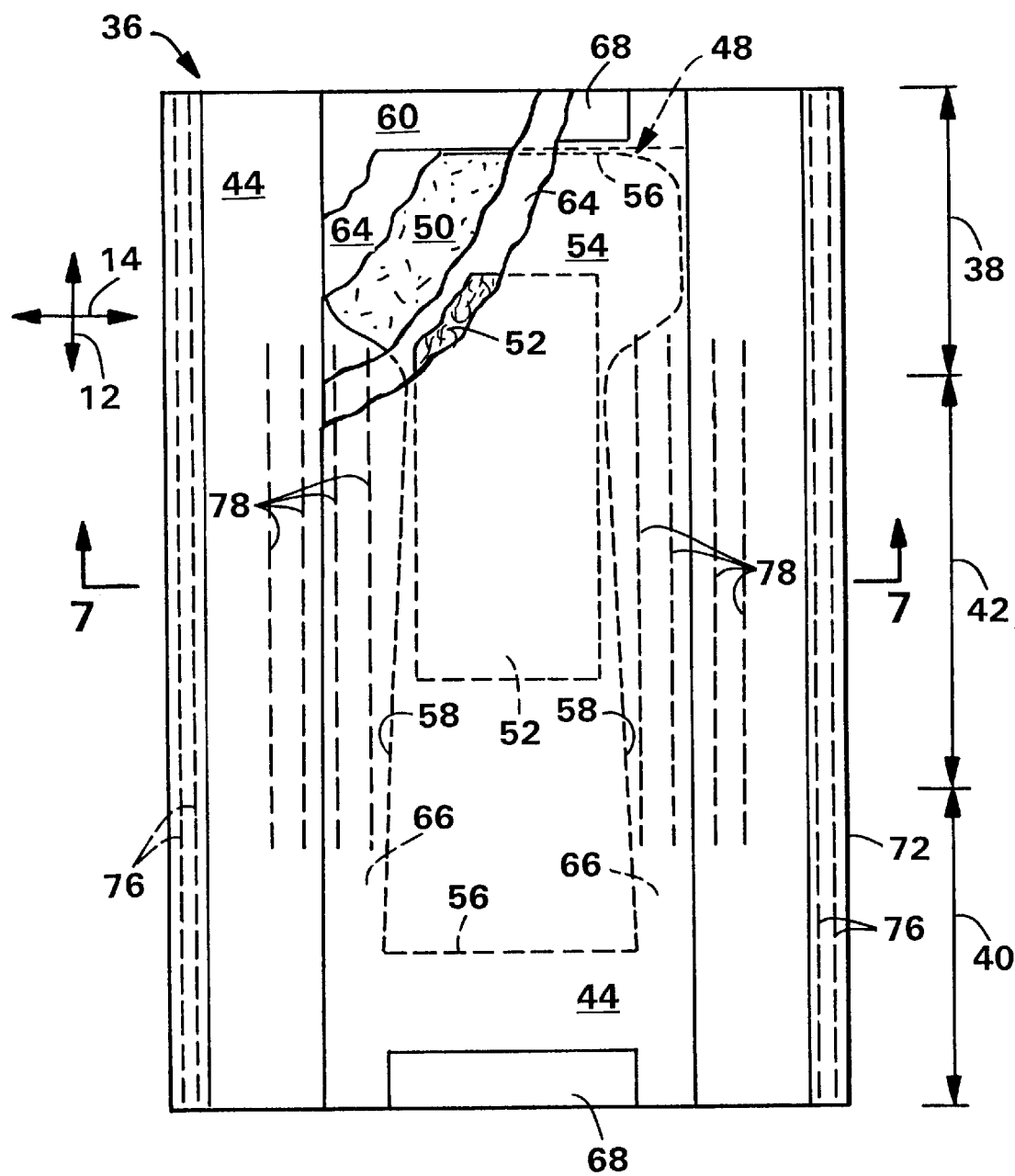
FIG. 6 representatively shows a partially cut away top plan view of a partially assembled absorbent assembly of the present invention.
Figure 7:
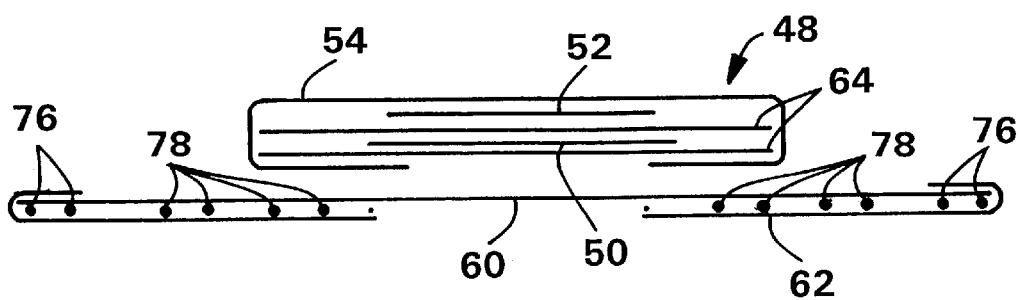
FIG. 7 representatively shows a schematic cross sectional view taken along line 7—7 of FIG. 6.

FIGS. 6 and 7 illustrate the absorbent assembly of FIGS. 4 and 5 in a partially assembled state prior to forming folded portions 70 by folding liquid impermeable member 44 around stiffening element 66. Further, FIG. 6 is a partially cutaway view illustrating the relative location of the various components of absorbent assembly 36.

Liquid impermeable member 44 is suitably formed from any flexible liquid impermeable material or a combination of materials which results in the combination being liquid impermeable. Suitable liquid impermeable materials are those liquid impermeable materials described for use in forming the outer cover. The liquid impermeable material 44 may be a single material such as a polyolefin film which may be either water vapor permeable or water vapor impermeable or, as illustrated in the figures, may be a laminate of two different materials. For example, the liquid impermeable material 44 may comprise a first liquid impermeable material 60 such as a polyolefin film or woven or nonwoven materials which have been treated to render them liquid impermeable, and a body contacting material 62 such as a nonwoven material. Specifically, the liquid impermeable member 44 may comprise a polypropylene film having a thickness of about 0.3 mil, which constitutes the first liquid impermeable material 60 and a polypropylene spunbond material joined thereto in the illustrated manner, which polypropylene spunbond material has a basis weight of about 0.6 ounce per square yard (20 grams per square meter), and is adapted to contact the skin of a wearer during use of the absorbent article of the present invention. In the absence of a body contacting material 62, the first liquid impermeable material would come into contact with the skin of a wearer. It is generally more comfortable that the skin of a wearer be exposed to a soft spunbond material rather than in direct contact with, for example, the liquid impermeable film.

The bodyside liner 54 presents a body-facing surface which is compliant, soft feeling, and nonirritating to a wearer's skin. Further, the bodyside liner 54 can be less hydrophilic than the retention portion 50, and is sufficiently porous to be liquid permeable, permitting liquid to penetrate through its thickness. A suitable bodyside liner 54 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Various woven and nonwoven fabrics can be used for bodyside liner 54. For example, the bodyside liner may be composed of a meltblown or spunbond web of polyolefin fibers. The bodyside liner may also be a bonded-carded web composed of natural and/or synthetic fibers. For the purposes of the present description, the term "nonwoven web" means a web of material which is formed without the aid of a textile weaving or knitting process.

The bodyside liner fabrics may be composed of a substantially hydrophobic and substantially nonwettable material, and the hydrophobic material may optionally be treated with a surfactant or otherwise processed to impart a desired level of wettability and hydrophilicity. In a particular embodiment of the invention, bodyside liner 54 can be a nonwoven, spunbond polypropylene fiber composed of about 2.8–3.2 denier fibers formed into a web having a basis weight of about 20 grams per square meter (gsm) and a density of about 0.13 grams per cubic centimeter. The fabric can be surface treated with a selected amount of surfactant, such as about 0.28 percent Triton X-102 surfactant available from Union Carbide, a business having offices in Danbury, Conn. The surfactant can be applied by any conventional means, such as spraying, printing, brush coating, or the like.

The absorbent core 48 is joined to said liquid impermeable member between said laterally opposed side margins of said liquid impermeable member. The absorbent core has a construction which is generally compressible, conformable, nonirritating to the wearer's skin, and capable of absorbing and retaining liquid body exudates. The absorbent core may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or noncoextensive, depending upon the requirements of the product. It is preferred, however, that each of the individual pieces be arranged in an operable, intimate contact along at least a portion of its boundary with at least one other adjacent piece of the absorbent core.

The absorbent core 48 may be manufactured in a wide variety of sizes and shapes (for example, rectangular, trapezoidal, T-shaped, I-shaped, hourglass shaped, etc.) and from a wide variety of materials. The size and absorbent capacity of the absorbent core 48 should be compatible with the size of the intended wearer and the liquid loading imparted by the intended use of the absorbent article. Further, the size and the absorbent capacity of the absorbent core 48 can be varied to accommodate wearer's ranging from infants through adults. In addition, it has been found that with the present invention, the densities and/or basis weights of the respective surge management portion 52 and retention portion 50, as well as their relative ratios, can be varied. In a particular aspect of the invention, the absorbent core has an absorbent capacity of at least about 300 grams of synthetic urine. Alternatively, the absorbent structure can have an absorbent capacity of at least about 400 grams of synthetic urine to provide improved performance.

Various types of wettable, hydrophilic fibrous materials can be used to form the component parts of absorbent core 48. Examples of suitable fibers include naturally occurring organic fibers composed of intrinsically wettable materials, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety, and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by aqueous liquids in contact with the fibers. The degree of wetting of the materials can, in turn, be described in terms of contact angles and the surface tensions of the liquid and materials involved. Equipment and techniques suitable for measuring the wettability of a particular fiber material or blends of fiber materials used for the absorbent core 48 can be provided by a Cahn, SFA-222 surface force analyzer system, or a substantially equivalent system. When measured with this system, fibers having contact angles of less than 90 degrees are designated "wettable" or hydrophilic, while fibers have contact angles of greater than 90 degrees are designated "nonwettable" or hydrophobic.

Retention portion 50 can comprise a matrix of hydrophilic fibers, such as a web of cellulosic fluff, mixed with particles of high-absorbency material. In particular arrangements, retention portion 50 may comprise a mixture of superabsorbent hydrogel forming particles and synthetic polymer meltblown fibers or a mixture of superabsorbent particles with a fibrous coform material comprising a blend of natural fibers and/or synthetic polymer fibers. The superabsorbent particles may be substantially homogeneously blended with the hydrophilic fibers or may be nonuniformly mixed. For example, the concentrations of superabsorbent particles may be arranged in non-stepwise gradient through a substantial portion of the thickness (Z-direction) of the absorbent core, with lower concentrations toward the bodyside of the absorbent core and relatively higher concentrations toward the outer side of the absorbent core. Suitable Z-gradient configurations are described in U.S. Pat. No. 4,699,823 issued Oct. 13, 1987, to Kellenberger et al., the disclosure of which is incorporated herein by reference in a manner that is consistent with the present description. The superabsorbent particles can also be arranged in a generally discrete layer within the matrix of hydrophilic fibers or may be configured at discrete, separate pocket regions of superabsorbent material. In addition, two or more different types of superabsorbent may be selectively positioned at different locations within or along the fiber matrix.

The high-absorbency material may comprise absorbent gelling materials, such as superabsorbents. The absorbent gelling material can be natural, synthetic, and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 50 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 50.

Preferred for use are particles having an average size of from about 20 microns to about 1 millimeter. "Particle size" as used herein means the weighted average of the smallest dimension of the individual particles.

An example of superabsorbent polymer suitable for use in the present invention is SANWET IM 3900 polymer available from Hoechst Celanese, a business having offices in Portsmouth, Va. Other suitable superabsorbents may include DOW DRYTECH 2035LD polymer obtained from Dow Chemical Co., a business having offices in Midland, Mich.; or FAVOR SAB 870M polymer available from Stockhausen, Inc., a business having offices in Greensboro, N.C.

The matrix of hydrophilic fibers comprising retention portion 50 may be a layer of cellulosic wood pulp fluff, and the particles of superabsorbent polymer can be distributed within the matrix of hydrophilic fibers. The hydrophilic fibers and high-absorbency particles can be provided in a fiber-to-particle ratio which is suitably not more than about 75:25, alternatively, is not more than about 70:30, and optionally, is not more than about 55:45, by weight. In further aspects of the invention, the fiber-to-particle ratio is suitably not less than about 25:75, preferably is not less than about 30:70 and more preferably is not less than about 45:55, by weight. Such fiber-to-particle ratios can be particularly desirable in the target zone (area of initial liquid application during use) of the absorbent structure. In particular embodiments of the invention, the fiber-to-particle weight ratio is not more than about 65:35 and is not less than about 50:50 to provide desired performance.

The hydrophilic fibers and high-absorbency particles can form an average composite basis weight which is within the range of about 400–900 gsm. Again, such basis weight is particularly desirable in the target zone of the absorbent structure. In certain aspects of the invention, the average composite basis weight is within the range of about 500–800 gsm, and preferably is within the range of about 550–750 gsm to provide desired performance.

To provide the desired thinness dimension to the various configurations of the absorbent article of the invention, retention portion 50 can be configured with a bulk thickness which is not more than about 0.6 cm. Preferably, the bulk thickness is not more than about 0.53 cm, and more preferably is not more than about 0.5 cm to provide improved benefits. The bulk thickness is determined under a restraining pressure of 0.2 psi (1.38 kPa).

The density of retention portion 50 or other component of the absorbent article can be calculated from its basis weight and thickness. With respect to diapers, for example, the weight and thickness are measured on newly unpacked, unfolded and dry diapers at a restraining pressure of 0.2 psi (1.38 kPa). Conventional thickness measuring devices may be employed to determine the thickness needed to calculate the density.

In the illustrated embodiments of the invention, absorbent retention portion 50 includes 4–22 grams of wood pulp fluff, preferably includes about 8–18 grams of fluff and more preferably includes about 12–14 grams of fluff to provide desired benefits. The wood pulp fluff generally provides shape and form to absorbent assembly 36, and carries and positions the particles of superabsorbent polymer or other high-absorbency material. Retention portion 50 can contain about 7–12 grams of superabsorbent polymer, and in the shown embodiment, contains about 8 grams of superabsorbent polymer. Sufficient superabsorbent polymer is incorporated into retention portion 50 to provide an adequate total absorbent capacity of at least about 300 gm of synthetic urine. For example, a medium size diaper for an infant weighing about 16–28 lb (about 7–13 kg) can typically have a total retention capacity of about 400 grams of synthetic urine.

The fluff and superabsorbent particles can be selectively placed into desired zones of retention portion 50. For example, the fluff basis weight may vary across the width dimension of retention portion 50. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material may be distributed down a medial region of retention portion 50 which extends along the length dimension of the retention portion and measures about 3.5–4.5 inches (about 8.9–11.4 cm) in width. In addition, the superabsorbent material may have a selected zoned placement to reduce the amount of superabsorbent material located proximate the side and end edges of the retention portion. The reduced amounts of superabsorbent material at the edges of the retention portion can improve the containment of the superabsorbent particles within the fibrous fluff matrix of retention portion 50. The pulsed, zoned placement of the superabsorbent material can, for example, be achieved by the method and apparatus described in U.S. Pat. No. 5,028,224 to C. Pieper et al., entitled METHOD AND APPARATUS FOR INTERMITTENTLY DEPOSITING PARTICULATE MATERIAL IN A SUBSTRATE and issued Jul. 2, 1991 (Attorney Docket No. 8761), the disclosure of which is hereby incorporated by reference in a manner that is consistent herewith.

The retention portion 50 can be overwrapped in a hydrophilic high wet-strength overwrap layer, such as a high wet-strength tissue or a synthetic fibrous web. Such overwrapping layer can also increase the in-use integrity of the retention portion. The overwrap layer can be suitably bonded, such as with adhesive, to adjacent components of the absorbent assembly.

Due to the high concentrations of superabsorbent particles, or other high-absorbency material, in retention portion 50, there can be an increased difficulty with regard to containing the high-absorbency particles within the retention portion and restricting the movement or migration of the superabsorbent onto the bodyside of the diaper. To improve the containment of the high-absorbency material, absorbent core 48 can include an improved overwrap placed immediately adjacent and around retention portion 50. The overwrap layer is preferably a layer of absorbent material which covers the major bodyside and outerside surfaces of the retention portion, and preferably encloses substantially all of the peripheral edges of the retention portion to form a substantially complete envelope thereabout. Alternatively, the overwrap layer can cover the major bodyside and outerside surfaces of the retention portion, and enclose substantially only the lateral side edges of the retention portion. Accordingly, lateral side edges of the overwrap layer would be closed about the retention portion. In such an arrangement, however, the end edges of the overwrap layer may not be completely closed around the end edges of the retention portion at the end portions of the article.

Overwrap layer 64 may comprise a multi-element wrapsheet which includes a separate bodyside overwrap layer and a separate outerside overwrap layer, each of which extends past all or some of the peripheral edges of retention portion 50, as representatively shown in FIGS. 2–7. Such a configuration of the overwrap layer can, for example, facilitate the formation of a substantially complete sealing and closure around the peripheral edges of retention portion 50.

The bodyside and outerside layers of overwrap layer 64 may be composed of substantially the same material, or may be composed of different materials. For example, the outerside layer of the overwrap layer may be composed of a relatively lower basis weight material having a relatively high porosity, such as a wet strength cellulosic tissue composed of softwood pulp. The bodyside layer of the overwrap layer may comprise one of the previously described overwrap layer materials which has a relatively low porosity. The low porosity bodyside layer can better prevent the migration of superabsorbent particles onto the wearer's skin, and the high porosity, lower basis weight outerside layer can help reduce costs and facilitate the processibility of the absorbent pad.

To provide the bonding between the bodyside and outerside portions of overwrap layer 64, an adhesive, such as NATIONAL STARCH 72-3723 adhesive, can be printed onto the appointed bonding areas of the overwrap with, for example, a rotogravure-type system. With alternative arrangements having an overwrap layer composed of a nonwoven meltblown fibrous web, the peripheral sealing of the bodyside and outerside layers may be accomplished by employing hot calendering to provide a sealed strip region around the periphery of the retention portion.

Due to the thinness of retention portion 50 and the high superabsorbent concentrations within the retention portion, the liquid uptake rates of the retention portion, by itself, may be too low, or may not be adequately sustained over multiple insults of liquid into the absorbent core. The addition of a porous, liquid-permeable layer of surge management material, however, can advantageously improve the overall uptake rate of the absorbent core. Surge management portion 52 is typically less hydrophilic than retention portion 50, and has an operable level of density and basis weight to quickly collect and temporarily hold liquid surges, to transport the liquid from its initial entrance point and to substantially completely release the liquid to other parts of the absorbent core 48 particularly retention portion 50. This configuration can help prevent the liquid from pooling and collecting on the portion of the absorbent assembly positioned against the wearers skin, thereby reducing the feeling of wetness by the wearer.

Various woven and nonwoven fabrics can be used to construct surge management portion 52. For example, the surge management portion may be a layer composed of a meltblown or spunbonded web of polyolefin fibers. The surge management portion may also be a bonded-cardedweb or an airlaid web composed of natural and synthetic fibers. The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inch. The surge management portion may be composed of a substantially hydrophobic material, and the hydrophobic material may optionally be treated with a surfactant or otherwise processed to impart a desired level of wettability and hydrophilicity.

Absorbent assembly 36 can include a surge management portion 52 which is arranged in a direct, contacting liquid communication with an adjacent absorbent retention portion 50. As representatively shown, surge management portion 52 may be configured for placement adjacent an outwardly facing, outerside of bodyside liner 54. Optionally, the surge management portion can be placed adjacent an inwardly facing, bodyside surface of bodyside liner 54. The shown configuration of the surge management portion is operably connected to the bodyside liner with a conventional pattern of adhesive, such as a swirl adhesive pattern. In addition, the surge management portion can be operably connected to the bodyside layer of overwrap layer 64 with a conventional pattern of adhesive. The amount of adhesive add-on should be sufficient to provide the desired levels of bonding, but should be low enough to avoid excessively restricting the movement of liquid from the bodyside layer, through the surge management portion and through the overwrap layer.

The retention portion 50 is positioned in liquid communication with surge management portion 52 to receive liquids released from the surge management portion, and to hold and store the liquid. In the shown embodiments, surge management portion 52 comprises a separate layer which is positioned over another, separate layer comprising the retention portion, thereby forming a dual-layer arrangement. The surge management portion serves to quickly collect and temporarily hold discharged liquids, to transport such liquids from the point of initial contact and spread the liquid to other parts of the surge management portion, and then to substantially completely release such liquids into the layer or layers comprising retention portion 50.

The representatively shown configuration of the surge management portion is substantially free of absorbent gelling material. Surge management portion 52 may, however, contain a very small amount of particulate gelling material to help acquire an initial liquid surge, but the amount should not be excessive.

As mentioned previously, surge management portion 52 can be a separately formed layer, which lies adjacent the outwardly facing surface of bodyside liner 54 between the retention portion and bodyside liner. Thus, surge management portion 52 need not comprise the entire thickness of absorbent core 48. The retention portion can optionally include a recess area which wholly or partially surrounds surge management portion 52, or the retention portion can be entirely positioned below the surge management portion. The arrangement which includes the recess in retention portion 50 can advantageously increase the area of contact and liquid communication between the retention portion and surge management portion 52. It should be understood, however, that surge management portion 52 could optionally be constructed to extend through the entire thickness of absorbent core 48 so that the capillary flow of liquid into retention portion 50 occurs primarily in a generally sideways (X-Y) direction.

The surge management portion can be of any desired shape consistent with the absorbency requirements of absorbent core 48. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 52 and retention portion 50 so that the relative capillarity difference between the portions can be fully utilized. In certain embodiments, for example, the surge management portion can be generally rectangular-shaped.

In the various configurations of the invention, surge management portion 52 may extend over the complete length of retention portion 50, or may extend over only a part of the retention portion length. Where the surge management portion extends only partially along the length of the retention portion, the surge management portion may be selectively positioned anywhere along absorbent core 48. For example, surge management portion 52 may function more efficiently when it is offset toward the front waistband of the garment and transversely centered within a front section of absorbent core 48. Thus, surge management portion 52 can be approximately centered about the longitudinal center line of absorbent core 48, and positioned primarily in a central region of a front section of the absorbent core 48.

In other aspects of the invention, the end edges of the surge management portion can be spaced longitudinally inboard from the end edges of the retention portion 50. In particular configurations of the invention, the corresponding, relatively adjacent front end edge of surge management portion 52 can be spaced a predetermined discrete distance from a front waistband end edge 56 of the retention portion 50.

It has been found that an effective fabric for constructing the surge management portion can be distinctively characterized by particular parameters. Such parameters include, for example, basis weight, permeability, porosity, surface area per void volume (SA/VV), compression resiliency and saturation capacity. Further parameters can include a bonding matrix which will help stabilize the pore size structure, and hydrophilicity. The bond-matrix and the blend of fiber deniers can advantageously provide for and substantially maintain a desired pore size structure.

Additional details regarding the surge materials and suitable techniques for determining the above-described parameters are set forth in U.S. patent application Ser. No. 08/206, 986 of C. Ellis and D. Bishop, entitled, FIBROUS NONWOVEN WEB SURGE LAYER FOR PERSONAL CARE ABSORBENT ARTICLES AND THE LIKE, and filed Mar. 4, 1994 (attorney docket No. 11,256); and U.S. patent application Ser. No. 08/206,069 of C. Ellis and R. Everett, entitled, IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); as well as U.S. Pat. No. 5,364,382 issued Nov. 15, 1994, to Latimer et al. and U.S. Pat. No. 5,429,629 issued Jul. 4, 1995, to Latimer et al., the disclosures of which are hereby incorporated by reference in a manner that is consistent herewith.

In desired configurations of the invention, the surge material can include natural fibers, synthetic fibers, such as synthetic polymer fibers, and combinations thereof. The fabric can, for example, be composed of polyolefin fibers, and in particular configurations the fibers can include bicomponent fibers. For example, polypropylene/polyethylene bicomponent fibers may be employed to form the bicomponent fiber portion of any of the described fabrics. In addition, the bicomponent fibers may be flat crimped or helically crimped.

Distal elastic members 76 and elastic members 78 can be attached, for example, to first liquid impermeable material 60 and/or body contacting materials 62 with suitable securing means, such as a selected pattern of adhesive or other type of bonding. For example, the adhesive may be applied by spraying adhesive, discontinuous droplets of filaments, and/or may be applied by arranging generally continuous lines of adhesive in a selected pattern, such as a swirl pattern. Alternatively, the elastic members 78 and distal elastic members 76 can be attached with a plurality of individual, longitudinally extending strips of adhesive. Each individual adhesive strip may be spatially separated from immediately adjacent adhesive strips by a discrete distance, and each individual adhesive strip may be arranged to attach substantially an individual one of the elastic members 78 or distal elastic members 76 to the first liquid impermeable material 60 and/or body contacting material 62.

The distal elastic members 76 are adapted to gather the distal edge of folded portion 70 to thereby position the distal edge away from the bodyside liner 54 in at least a portion of the intermediate portion of the absorbent assembly 36. Accordingly, while in the illustrated embodiment the distal elastic members 76 are illustrated as extending along the entire length of the distal edge 72 of folded portion 70, the distal elastic member 76 may be located only along a portion of the length of the distal edge 72.

Elastic members 78 are adapted to contract and gather at least a portion of the intermediate portion 42 of absorbent assembly 36. In use, this results in the intermediate portion 42 of absorbent assembly 36 maintaining a close fit about the leg and/or thigh of a wearer during use.

In the illustrated embodiment, elastic members 78 are illustrated as extending along less than the entire length of absorbent assembly 36. It is generally desired that the elastic members 78 extend along at least a major portion of the intermediate portion 42 of absorbent assembly 36. It is, of course, possible for the elastic members 78 to extend along the entire length of absorbent assembly 36.

In the illustrated embodiment, there are two distal elastic members 76 illustrated. It is, of course, possible to employ a single distal elastic member or to employ multiple distal elastic members. Similarly, all of the distal elastic members may extend the same length along the absorbent assembly 36 or may extend along different lengths of absorbent assembly 36.

In a like manner, while in the illustrated embodiment there are four elastic members 78 illustrated, it is possible to employ between 0 and about 15 or more elastic members. The elastic members 78 may all extend along the same length of absorbent assembly 36 or may extend along different lengths of absorbent assembly 36. The spacing of elastic members 78 from one another and from the distal elastic members is widely variable. In essence, the elastic members 78 may be located any where in absorbent assembly 36 that allows them to perform the desired function. While distal elastic members 76 and elastic members 78 are illustrated as being directly attached to either the first liquid impermeable material 60 or the body contacting materials 62, it is also possible to attach the distal elastic members 76 or elastic members 78 to a separate flexible sheet of material which is, in turn, attached to the absorbent assembly 36. Distal elastic members 76 and elastic members 78 are illustrated as being generally parallel to one another and to a longitudinal central axis of absorbent assembly 36. It is to be understood that nonparallel orientations such as curved orientations are possible.

A suitable material for use as distal elastic members 76 or elastic members 78 is a 470 decitex LYCRA elastomeric strand which is available from E. I. du Pont Nemours, a business having offices in Wilmington, Del. Alternatively, elastic strands may be composed of 700 denier Glospan S7 spandex elastomer, which is available from Globe Manufacturing, a business having offices in Fall River, Mass. Other elastomeric materials such as elastomeric foam or nonwoven materials or elastomeric pressure sensitive adhesives are also suitable for use as distal elastic members 76 or elastic members 78.

Figure 8:
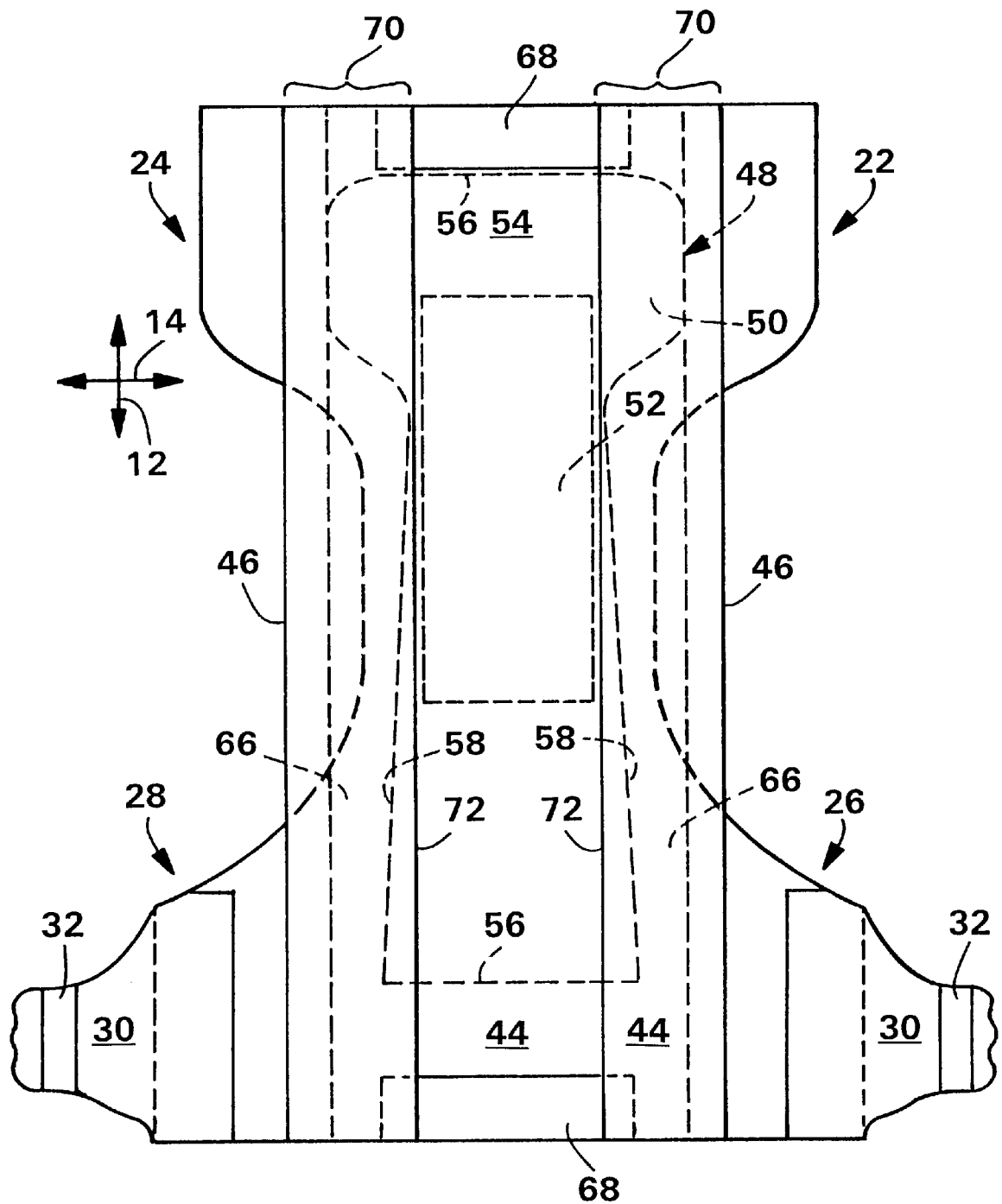
FIG. 8 representatively shows a top plan view of an absorbent article according to the present invention incorporating the outer cover of FIG. 1 and the absorbent assembly of FIG. 2.
Figure 9:
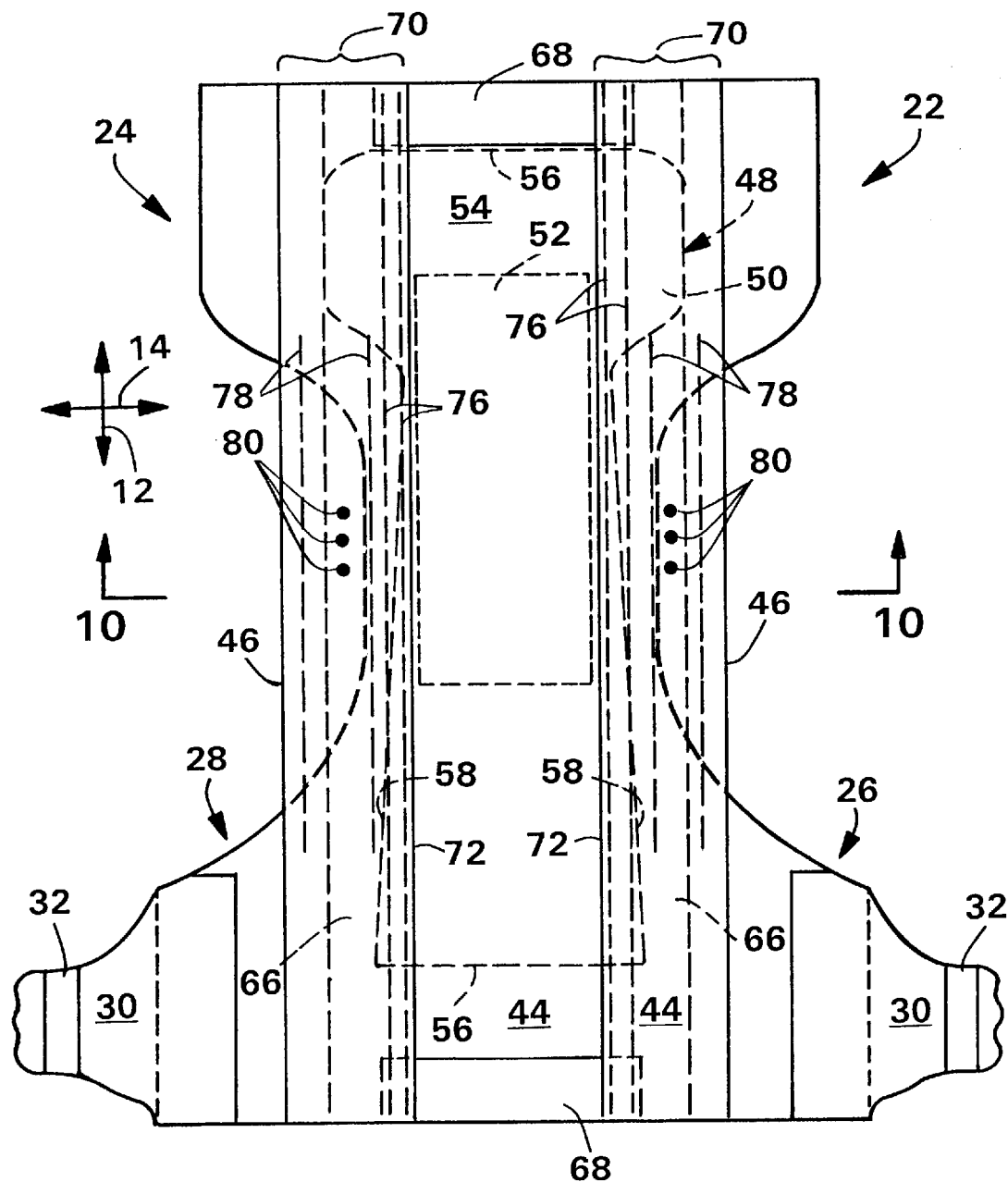
FIG. 9 representatively shows a top plan view of an absorbent article according to the present invention employing the outer cover of FIG. 1 and the absorbent assembly of FIG. 4.

FIG. 8 illustrates the absorbent assembly illustrated in FIG. 2 joined to the outer cover illustrated in FIG. 1. Similarly, FIG. 9 illustrates the absorbent assembly of FIG. 4 joined to the outer cover of FIG. 1. The elastic members 76 and 78 are suitably allowed to relax before the absorbent assembly is joined to the outer cover.

Figure 10:
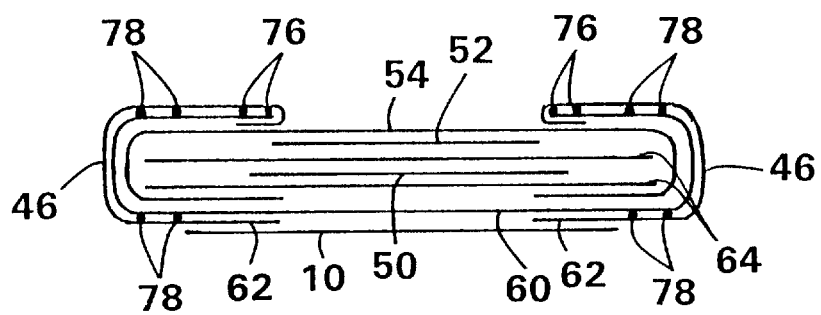
FIG. 10 representatively shows a schematic cross sectional view taken along line 10—10 of FIG. 9.

FIG. 10 is a schematic cross-sectional view taken along line 10—10 of FIG. 9. As can be seen from reference to FIGS. 8–10, the absorbent assembly may be coterminous with the outer cover. Of course, it is also possible for the absorbent assembly to have a length which is greater than the outer cover or which is less than the outer cover. The absorbent assembly is suitably adhesively attached to the outer cover. Other methods of joining the absorbent assembly to outer cover 10 may suitably be employed.

In some instances, it may be desirable to attach a portion of the intermediate portion 42 of folded portion 70 to the bodyside liner 54. Such attachment may be desirable to keep folded portions 70 from overlapping one another in the intermediate (crotch) portion. For example, with reference to FIG. 9, attachments points 80 may attach the folded portion 70 to bodyside liner 54 in the intermediate portion of folded portion 70. Suitable methods of forming attachment points 80 include adhesive bonding and thermal bonding such as ultrasonic bonding.

EXAMPLES

Water Vapor Transmission Rate—A suitable technique for determining the WVTR (water vapor transmission rate) value of a material is as follows. For the purposes of the present invention, 3-inch diameter (76 millimeter) circular samples are cut from the test material and from a control material, Celguard® 2500 (Hoechst Celanese Corporation). Two or three samples are prepared for each material. Test cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred milliliters of distilled water are poured into each Vapometer cup, and each of the individual samples of the test materials and control material are placed across the open top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.). The oven is a constant temperature oven with external air circulating through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary, test WVTR value is calculated as follows:

$$\text{Test } WVTR = \frac{[(\text{grams weight loss over 24 hours}) \times 7571]}{24} (g/m^2/24 \text{ hours})$$

The relative humidity within the oven is not specifically controlled. Under predetermined set conditions of 100° F. and ambient relative humidity, the WVTR for Celguard 2500 has been determined to be 5000 g/m²/24 hours. Accordingly, Celguard 2500 is run as a control sample with each test. Celguard 2500 is a 0.0025 cm thick film composed of a microporous polypropylene.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

What is claimed is:

1. A disposable absorbent article having a longitudinal length dimension, a lateral width dimension, a front portion, a rear portion, and an intermediate portion which interconnects said front and rear portions, said article comprising:
   an outer cover having a longitudinal length dimension, a lateral width dimension, a front portion, a rear portion, and an intermediate portion which interconnects said front and rear portions, at least one of said front and rear portions of said outer cover having a lateral width dimension greater than a lateral width dimension of said intermediate portion of said outer cover to define ear portions; and
   an absorbent assembly joined to said outer cover, said absorbent assembly having a longitudinal length dimension, a lateral width dimension, a front portion, a rear portion, and an intermediate portion which interconnects said front and rear portions, said absorbent assembly comprising:
      a liquid impermeable member having a pair of laterally opposed side margins defining the lateral width of said absorbent assembly in said intermediate portion of said absorbent assembly, which lateral width is greater than the lateral width of said outer cover in said intermediate portion of said outer cover; and
      an absorbent core joined to said liquid impermeable member between said laterally opposed side margins of said liquid impermeable member.

2. The article of claim 1 further comprising fastening means joined to said outer cover for fastening said article about the waist of a wearer.

3. The article of claim 1 wherein said outer cover is water vapor permeable.

4. The article of claim 3 wherein said outer cover has a water vapor transmission rate of from about 200 to about 8000 grams per square meter per 24 hours.

5. The article of claim 1 wherein said outer cover defines ear portions on said rear portion.

6. The article of claim 1 wherein said outer cover defines ear portions on both said front and rear portions.

7. The article of claim 1 wherein the laterally opposed side margins of said liquid impermeable member are elasticized.

8. The article of claim 7 wherein the laterally opposed side margins of said liquid impermeable member are elasticized with a plurality of elastic strands joined to said liquid impermeable member.

9. The article of claim 1 or 7 wherein said laterally opposed side margins of said liquid impermeable member are defined by longitudinal fold lines which define folded portions having longitudinal end portions, an intermediate portion between said longitudinal end portions, and a distal edge, said longitudinal end portions being joined to said absorbent assembly in said front and rear portion of said absorbent assembly intermediate the lateral width dimension of said absorbent assembly.

10. The article of claim 9 wherein said distal edge of said folded portion is unjoined to said absorbent assembly in at least a portion of said intermediate portion of said folded portion.

11. The article of claim 10 wherein said distal edge is elasticized such that the folded portions form a containment pocket.

12. The article of claim 9 wherein a fibrous layer is joined to said folded portions and forms a body contacting surface.

13. The article of claim 1 wherein said absorbent core comprises a retention portion having a longitudinal length dimension defined by end margins and a lateral width dimension defined by side margins for absorbing and retaining liquid and a bodyside liner which at least partially covers said retention portion.

14. The article of claim 13 wherein said retention portion is at least partially enclosed by an overwrap layer and said bodyside liner partially covers said retention portion and said overwrap layer.

15. The article of claim 14 wherein said bodyside liner extends laterally beyond said side margins of said retention portion to define stiffening elements.

16. The article of claim 15 wherein said bodyside liner extends laterally beyond said side margins of said retention portion by at least about 12 millimeters to define said stiffening elements.

17. The article of claim 16 wherein portions of said stiffening elements are not directly joined to said liquid impermeable member so as to be movable with respect thereto.

18. The article of claim 17 wherein said overwrap layer and said bodyside liner extend laterally beyond longitudinal side margins of said retention portion to define stiffening elements.

19. The article of claim 15, 16, 17, or 18 wherein said laterally opposed side margins of said liquid impermeable member are defined by longitudinal fold lines which define folded portions having longitudinal end portions, an intermediate portion between said longitudinal end portions, and a distal edge, said longitudinal end portions being joined to said absorbent assembly in said front and rear portion of said absorbent assembly intermediate the lateral width dimension of said absorbent assembly.

20. A disposable absorbent article having a longitudinal length dimension, a lateral width dimension, a front portion, a rear portion, and an intermediate portion which interconnects said front and rear portions, said article comprising:
   an outer cover having a longitudinal length dimension, a lateral width dimension, a front portion, a rear portion, and an intermediate portion which interconnects said front and rear portions, at least one of said front and rear portions of said outer cover having a lateral width dimension greater than a lateral width dimension of said intermediate portion of said outer cover to define ear portions;
   an absorbent assembly joined to said outer cover, said absorbent assembly having a longitudinal length dimension, a lateral width dimension, a front portion, a rear portion, and an intermediate portion which interconnects said front and rear portions, said absorbent assembly comprising:
- a liquid impermeable member having a pair of laterally opposed side margins defining the lateral width of said absorbent assembly in said intermediate portion of said absorbent assembly, which lateral width is greater than the lateral width of said outer cover in said intermediate portion of said outer cover, said laterally opposed side margins of said liquid impermeable member being defined by longitudinal fold lines which form folded portions having longitudinal end portions, an intermediate portion between said longitudinal end portions, and a distal edge, said longitudinal end portions being joined to said absorbent assembly in said front and rear portion of said absorbent assembly intermediate the lateral width dimension of said absorbent assembly; and
- an absorbent core joined to said liquid impermeable member between said laterally opposed side margins of said liquid impermeable member; and fastening means joined to said outer cover for fastening said article about the waist of a wearer.

21. The article of claim 20 wherein said outer cover is water vapor permeable.

22. The article of claim 21 wherein said outer cover has a water vapor transmission rate of from about 200 to about 8000 grams per square meter per 24 hours.

23. The article of claim 20 wherein said outer cover defines the ear portions on said rear portion.

24. The article of claim 20 wherein said outer cover defines ear portions on both said front and rear portions.

25. The article of claim 20 wherein the laterally opposed side margins of said liquid impermeable member are elasticized.

26. The article of claim 25 wherein the laterally opposed side margins of said liquid impermeable member are elasticized with a plurality of elastic strands joined to said liquid impermeable member.

27. The article of claim 20 wherein said distal edge of said folded portion is unjoined to said absorbent assembly in at least a portion of said intermediate portion of said folded portion.

28. The article of claim 27 wherein said distal edge is elasticized such that the folded portions form a containment pocket.

29. The article of claim 20 wherein said absorbent core comprises a retention portion having a longitudinal length dimension defined by end margins and a lateral width dimension defined by side margins for absorbing and retaining liquid and a bodyside liner which at least partially covers said retention portion.

30. The article of claim 29 wherein said retention portion is at least partially enclosed by an overwrap layer and said bodyside liner partially covers said retention portion and said overwrap layer.

31. The article of claim 29 wherein said bodyside liner extends laterally beyond longitudinal side margins of said retention portion to define stiffening elements.

32. The article of claim 31 wherein said bodyside liner extends laterally beyond longitudinal side margins of said retention portion by at least about 12 millimeters to define said stiffening elements.

33. The article of claim 32 wherein portions of said stiffening elements are not directly joined to said liquid impermeable member so as to be movable with respect thereto.

34. The article of claim 31 wherein said overwrap layer and said bodyside liner extend laterally beyond longitudinal side margins of said retention portion to define stiffening elements.

* * * * *